(12) United States Patent
Abe et al.

(10) Patent No.: US 6,541,657 B2
(45) Date of Patent: Apr. 1, 2003

(54) UNSATURATED CARBOXYLATE AND ITS PRODUCTION PROCESS AND USE

(75) Inventors: Kazuaki Abe, Suita (JP); Keiichiro Mizuta, Takatsuki (JP); Rie Inoue, Nara (JP)

(73) Assignee: Nippon Shokubai Co., Ltd, Osaka (JP)

( * ) Notice: Subject to any disclaimer, the term of this patent is extended or adjusted under 35 U.S.C. 154(b) by 88 days.

(21) Appl. No.: 09/811,121

(22) Filed: Mar. 17, 2001

(65) Prior Publication Data

US 2001/0051744 A1 Dec. 13, 2001

(30) Foreign Application Priority Data

Mar. 24, 2000 (JP) ........................................ 2000-085193

(51) Int. Cl.[7] .......................... C07C 67/26; C07C 69/52; C09K 3/00
(52) U.S. Cl. .................... 560/209; 560/225; 252/182.18
(58) Field of Search .................................. 560/209, 225, 560/244; 252/182.18

(56) References Cited

U.S. PATENT DOCUMENTS

| 5,189,199 A | | 2/1993 | Godleski |
| 5,409,764 A | * | 4/1995 | Otsuki et al. ............... 428/221 |
| 5,869,590 A | | 2/1999 | Clark et al. |

FOREIGN PATENT DOCUMENTS

| DE | 44 29 690 A1 | 3/1995 |
| GB | 1407813 | 9/1975 |
| JP | 5-32721 A | 2/1993 |
| JP | 2774122 B2 | 4/1998 |

OTHER PUBLICATIONS

"Vorkommen neuer bifunktioneller Ester im Romisch–Kamillenol (Anthemis nobilis I.)" Klimes et al, Helv. Chim. Acta, vol. 64 fasc.7, pp. 2238–2249 (1981).*
"Study on Roman Chamomile (Chamaemelum nobile L. All.) Oil" Antonelli and Fabbri, J. Essent. Oil. Res., vol. 10, pp. 571–574 (1998).*
"An Ascending Synthesis of Adrenalcorticosteroids. The Total synthesis of (+)–Androsterone" Dzierba et al. J. Am. Chem. Soc vol. 118, pp. 4711–4712 (1996).*

* cited by examiner

Primary Examiner—Mukund J. Shah
Assistant Examiner—Zachary C. Tucker
(74) Attorney, Agent, or Firm—Haugen Law Firm, PLLP (57) ABSTRACT

The present invention provides: an unsaturated carboxylate which has both an unsaturated group and a hydroxyl group, and is applicable to a wide range of crosslinking processes, and has moderate polymerizability, and has a novel specific structure; and a production process which enables to obtain this unsaturated carboxylate without causing the rearrangement of the carbon-carbon unsaturated bond of the raw unsaturated oxirane, and gives a high production ratio of unsaturated oxirane-1-mol adduct. A reaction of a specific unsaturated carboxylic acid with a specific unsaturated oxirane is carried out using at least one catalyst selected from the group consisting of chromium compounds, manganese compounds, iron compounds, nickel compounds, zinc compounds, silver compounds, tin compounds, neodymium compounds, and lead compounds, thereby obtaining an unsaturated carboxylate of general formula (1).

3 Claims, 4 Drawing Sheets

UNSATURATED CARBOXYLATE AND ITS PRODUCTION PROCESS AND USE

BACKGROUND OF THE INVENTION

A. Technical Field

The present invention relates to a novel unsaturated carboxylate and its production process and use.

B. Background Art

Hitherto, unsaturated carboxylates which have an unsaturated group or hydroxyl group in moieties derived from alcohol components of the esters are widely used for purposes of such as paints and crosslinking agents.

Allyl methacrylate is known as an example of the unsaturated carboxylates which have the unsaturated group. However, allyl methacrylate has a nonsubstituted allyl group which is highly reactive. Therefore, allyl methacrylate undergoes gelation in polymerization reactions so easily as not to fit into use for the purpose of post-crosslinking. Incidentally, herein the nonsubstituted allyl group means an allyl group in which only hydrogen atoms are bonded to all carbon atoms.

On the other hand, hydroxyethyl (meth)acrylate and hydroxypropyl (meth)acrylate are known as examples of the unsaturated carboxylates which have the hydroxyl group. These can, for example, be treated by polymerizing their unsaturated carboxylic acid moieties and then crosslinking their hydroxyl group moieties using such as diisocyanates. However, such a treatment can be carried out only in the case where the reactivity of the hydroxyl group is available, therefore their applicable uses are naturally limited.

Unsaturated carboxylates having both an allylic unsaturated group and a hydroxyl group are disclosed as those for which the crosslinking methods can be expected to widely be selected. For example, British Patent No. 1407813 proposes a compound obtained by a reaction of methacrylic acid with allyl glycidyl ether. However, this compound also has the nonsubstituted allyl group and therefore has the same problems as those mentioned above.

A compound which is obtained by causing an unsaturated oxirane to react instead of the above-mentioned allyl glycidyl ether is also proposed. For example, Japanese Patent No. 2774122 and German Patent No. 4429690 propose processes for synthesizing a carboxylate having a carbon-carbon unsaturated group by carrying out a reaction of a carboxylic acid with an unsaturated oxirane. However, as to these processes, the carbon-carbon unsaturated group is directly bonded to a carbon atom of the oxirane ring, therefore the addition reaction of the carboxylic acid runs not only by 1,2-addition reaction, but also by 1,4-addition reaction simultaneously therewith. A carboxylate resultant from this 1,4-addition reaction has a rearranged inner olefin structure in its oxirane-derived moiety and is therefore so much low reactive as not to be fit for purposes of such as crosslinking. Furthermore, according to J. Chem. Soc. Chem. Comm., (1972) p. 491 and J. Am. Chem. Soc., (1953) vol. 75, p. 3496, it is known that if Lewis acids such as rhodium complexes and boron trifluoride are used, an rearrangement of the unsaturated oxirane itself easily arises to form an unsaturated aldehyde or ketone.

On the other hand, JP-A-032721/1993 discloses a vinyl-group-containing unsaturated carboxylate composition which is obtained by a process including the step of carrying out a reaction of a compound having one or more vinyl groups and one epoxy group per molecule with an unsaturated carboxylic acid. However, this process produces not only a 1-mol adduct, but also a large amount of multiple-mol adducts, wherein the 1-mol adduct is a product by addition of 1 mol of the compound having one or more vinyl groups and one epoxy group per molecule to the unsaturated carboxylic acid, and wherein the multiple-mol adducts are products by addition of at least 2 mol of the compound having one or more vinyl groups and one epoxy group per molecule to the unsaturated carboxylic acid, therefore the resultant unsaturated carboxylate composition is a mixture containing the multiple-mol adducts in a high ratio. These multiple-mol adducts have the disadvantage, for example, of giving higher viscosity and more easily gelling than the 1-mol adduct. Therefore, the unsaturated carboxylate composition containing the multiple-mol adducts in a high ratio, as disclosed in the above publication, is difficult to practically use according to uses. Furthermore, the above publication does not specifically describe the structure of the unsaturated carboxylate or the production ratio between the above 1-mol and multiple-mol adducts in the unsaturated carboxylate composition.

SUMMARY OF THE INVENTION

A. Object of the Invention

An object of the present invention is to provide: an unsaturated carboxylate which has both an unsaturated group and a hydroxyl group, and is applicable to a wide range of crosslinking processes, and has moderate polymerizability, and has a novel specific structure; a production process which enables to obtain this unsaturated carboxylate without causing the rearrangement of the carbon-carbon unsaturated bond of the raw unsaturated oxirane, and gives a high production ratio of unsaturated carboxylate that is a product by addition of 1 mol of the unsaturated oxirane to the unsaturated carboxylic acid (such an unsaturated carboxylate might herein be referred to simply as "1-mol adduct"); and a radical-curable resin composition containing this unsaturated carboxylate.

B. Disclosure of the Invention

The present inventors diligently studied to solve the above-mentioned problems. As a result, they have completed the present invention by finding that if the unsaturated carboxylate possesses two unsaturated groups having different reactivities as well as a hydroxyl group formed by ring-opening of an oxirane ring wherein, of the unsaturated groups, the unsaturated group in the alcohol component moiety of the ester is a substituted allyl group or a homoallyl group, then such an unsaturated carboxylate displays moderate polymerizability and is applicable to a wide range of crosslinking processes, and further that if at least one catalyst selected from the group consisting of chromium compounds, manganese compounds, iron compounds, nickel compounds, zinc compounds, silver compounds, tin compounds, neodymium compounds, and lead compounds is used in a reaction between an unsaturated oxirane having a specific structure and an unsaturated carboxylic acid having a specific structure, then the rearrangement of the carbon-carbon unsaturated bond of the raw unsaturated oxirane can be inhibited, and further the 1-mol adduct can efficiently be obtained.

Namely, an unsaturated carboxylate, according to the present invention, is represented by the following general formula (1):

(1)

wherein:
R¹ and R² independently of each other represent a hydrogen atom or an organic residue;
R³ represents a hydrogen atom, a methyl group, or an organic residue other than the methyl group;
n is an integer of not smaller than 1; and
X represents:

wherein:
R⁴ to R⁹ independently of each other represent a hydrogen atom or an alkyl group;
wherein the ratio of a 1-mol adduct of n=1 in the general formula (1) to the total of a 2-mol adduct of n=2 in the general formula (1) and a 3-mol adduct of n=3 in the general formula (1) satisfies the following inequality:

(1-*mol adduct*)/{(2-*mol adduct*)+(3-*mol adduct*)} ≧ 1(*molar ratio*).

A production process for an unsaturated carboxylate, according to the present invention, comprises the step of carrying out a reaction of an unsaturated carboxylic acid of general formula (2) below with an unsaturated oxirane of general formula (3) below using at least one catalyst selected from the group consisting of chromium compounds, manganese compounds, iron compounds, nickel compounds, zinc compounds, silver compounds, tin compounds, neodymium compounds, and lead compounds,
wherein the general formula (2) is:

(2)

wherein:
R¹ and R² independently of each other represent a hydrogen atom or an organic residue; and
R³ represents a hydrogen atom, a methyl group, or an organic residue other than the methyl group;
and wherein the general formula (3) is:

(3)

wherein:
R⁴ to R⁹ independently of each other represent a hydrogen atom or an alkyl group.

A radical-curable resin composition, according to the present invention, comprises a radical-curable resin and further comprises at least the above unsaturated carboxylate according to the present invention as a reactive diluent.

These and other objects and the advantages of the present invention will be more fully apparent from the following detailed disclosure.

DETAILED DESCRIPTION OF THE INVENTION

Hereinafter, the unsaturated carboxylate and its production process and use, according to the present invention, are described in order and in detail.

(Unsaturated Carboxylate):

The unsaturated carboxylate, according to the present invention, is a novel compound which, as is represented by the aforementioned general formula (1), has both an unsaturated group and a hydroxyl group.

In the aforementioned general formula (1), R¹ and R² independently of each other represent a hydrogen atom or an organic residue, and R³ represents a hydrogen atom, a methyl group, or an organic residue other than the methyl group, n is an integer of not smaller than 1, and X represents:

(hereinafter abbreviated to x1) or (hereinafter abbreviated to x2) wherein R⁴ to R⁹ independently of each other represent a hydrogen atom or an alkyl group. The aforementioned organic residue is not especially limited, but examples thereof include: hydrocarbon groups, such as saturated or unsaturated aliphatic ones, saturated or unsaturated alicyclic ones, and aromatic ones; halogen groups; a hydroxyl group; ether groups; sulfide groups; a nitrile group; an aldehyde group; a carboxyl group; a sulfonic acid group; ester groups; and amide groups. Of these groups, particularly, the aforementioned hydrocarbon groups, carboxyl group, ester groups and amide groups are favorable. In addition, the aforementioned alkyl group is not especially limited, but specific examples thereof include methyl, ethyl, propyl, and butyl.

In this way, as to the unsaturated carboxylate according to the present invention, its polymerizability is an improved one, because this unsaturated carboxylate possesses two unsaturated groups having different reactivities wherein, of the unsaturated groups, the unsaturated group in the alcohol component moiety of the ester is a substituted allyl group or a homoallyl group. Furthermore, this unsaturated carboxylate is applicable to a wide range of crosslinking processes because of possession of a hydroxyl group having reactivity different from that of the above unsaturated groups. Therefore, this unsaturated carboxylate is a useful substance for various uses. Incidentally, herein the substituted allyl group means an allyl group in which at least one organic residue besides hydrogen atoms is bonded to a carbon atom. For example, the unsaturated carboxylate is applicable to uses for the purpose of post-crosslinking, such as crosslinking agents, by utilizing the advantage in that, of the polymerizable unsaturated groups, the substituted allyl group or homoallyl group as mentioned above has so moderately low polymerizability as to be difficult to gelate when polymerizing the unsaturated carboxylic acid moiety.

The unsaturated carboxylate, according to the present invention, is obtainable by the below-mentioned production process according to the present invention, and is usually obtained as a mixture of an unsaturated carboxylate in which X in the aforementioned general formula (1) is the aforementioned x1 with an unsaturated carboxylate in which X in the aforementioned general formula (1) is the aforementioned x2. Therefore, the unsaturated carboxylate according to the present invention may comprise such a mixture. In such a case, the ratio of the unsaturated carboxylate in which X is the aforementioned x1 is favorably not less than 10 mol %, namely, (unsaturated carboxylate in which X is x1):(unsaturated carboxylate in which X is x2)=10:90 to 100:0 (molar ratio), more favorably (unsaturated carboxylate in which X is x1):(unsaturated carboxylate in which X is x2)=30:70 to 90:10 (molar ratio), still more favorably (unsaturated carboxylate in which X is x1):(unsaturated carboxylate in which X is x2)=50:50 to 80:20 (molar ratio). The unsaturated carboxylate according to the present invention has both the polymerizability-improved unsaturated group and a hydroxyl group in the alcohol component moiety of the ester, but the unsaturated carboxylate in which X is the aforementioned x1 has a more reactive primary alcohol and is therefore, for example, advantageous when the hydroxyl group moiety is crosslinked using such as diisocyanates or acid anhydrides. In the case where the ratio of the unsaturated carboxylate in which X is the aforementioned x1 is less than 10 mol %, it is difficult to sufficiently display such advantageous reactivity of the hydroxyl group.

In addition, as to the unsaturated carboxylate according to the present invention, it is important that the ratio of a 1-mol adduct of n=1 in the aforementioned general formula (1) to the total of a 2-mol adduct of n=2 in the aforementioned general formula (1) and a 3-mol adduct of n=3 in the aforementioned general formula (1) satisfies the following inequality: (1-mol adduct)/{(2-mol adduct)+(3-mol adduct)}$\geq$1 (molar ratio). The unsaturated carboxylate, according to the present invention, is obtainable by a ring-opening addition reaction of the unsaturated oxirane to the unsaturated carboxylic acid, but, usually, in this ring-opening addition reaction, it is so difficult to control the molar number of the addition of the unsaturated oxirane (i.e. n in general formula (1)) to 1 mol that this reaction by-produces a large amount of multiple-mol adducts (particularly, 2-mol adduct and 3-mol adduct) which are products by addition of at least 2 mol of the unsaturated oxirane to the unsaturated carboxylic acid. In addition, 4-mol or more multiple-mol adducts might form. However, the below-mentioned production process can give the aimed 1-mol adduct so selectively that the unsaturated carboxylate according to the present invention as obtained by this process satisfies (1-mol adduct)/{(2-mol adduct)+(3-mol adduct)}$\geq$1 (molar ratio), favorably (1-mol adduct)/{(2-mol adduct)+(3-mol adduct)}$\geq$2 (molar ratio), more favorably (1-mol adduct)/{(2-mol adduct)+(3-mol adduct)}$\geq$4 (molar ratio), still more favorably (1-mol adduct)/{(2-mol adduct)+(3-mol adduct)}$\geq$9 (molar ratio), most favorably (1-mol adduct)/{(2-mol adduct)+(3-mol adduct)}$\geq$19 (molar ratio). In the case where the total of the 2-mol adduct and the 3-mol adduct is more than the above range, there are problems of such as high viscosity and easy gelation, therefore the use is substantially difficult.

The unsaturated carboxylate according to the present invention is a substance having both an unsaturated group and a hydroxyl group, and the unsaturated group present in the alcohol component moiety of the ester has moderate polymerizability and is therefore applicable to a wide range of crosslinking processes along with the hydroxyl group. Therefore, the unsaturated carboxylate can favorably be utilized for uses such as paints, crosslinking agents, adhesives, resin reformers, and reactive diluents.

(Production Process for Unsaturated Carboxylate):

In the present invention production process for an unsaturated carboxylate, the reaction of the unsaturated carboxylic acid of the aforementioned general formula (2) with the unsaturated oxirane of the aforementioned general formula (3) is carried out using at least one catalyst selected from the group consisting of chromium compounds, manganese compounds, iron compounds, nickel compounds, zinc compounds, silver compounds, tin compounds, neodymium compounds, and lead compounds.

In the present invention, specific examples of the unsaturated carboxylic acid of the aforementioned general formula (2) include: unsaturated monocarboxylic acids, such as acrylic acid, methacrylic acid, crotonic acid, tiglic acid, angelic acid, senecioic acid, 2-hexenoic acid, sorbic acid, and cinnamic acid; unsaturated dicarboxylic acids, such as maleic acid, fumaric acid, itaconic acid, and muconic acid; half esters of unsaturated dicarboxylic acids such as maleic acid, fumaric acid, itaconic acid, and muconic acid (e.g. methyl ester, ethyl ester, n-propyl ester, iso-propyl ester, n-butyl ester, iso-butyl ester, 2-ethylhexyl ester, cyclohexyl ester, cyclohexylmethyl ester, phenyl ester, and benzyl ester of each dicarboxylic acid); and half amides of unsaturated dicarboxylic acids such as maleic acid, fumaric acid, itaconic acid, and muconic acid (e.g. methylamide, dimethylamide, ethylamide, diethylamide, n-butylamide, di-n-butylamide, iso-butylamide, cyclohexylamide, cyclohexylmethylamide, anilide, and benzylamide of each dicarboxylic acid). Of these acids, particularly, acrylic acid, methacrylic acid, maleic acid and fumaric acid are favorable, and acrylic acid and methacrylic acid are more favorable, and acrylic acid is the most favorable.

In the present invention, specific examples of the unsaturated oxirane of the aforementioned general formula (3) include: 1,2-epoxy-3-butene, 1,2-epoxy-2-methyl-3-butene, 1,2-epoxy-3-methyl-3-butene, 1,2-epoxy-3-pentene, 2,3-epoxy-4-pentene, 1,2-epoxy-4-methyl-3-pentene, and 2,3-epoxy-2-methyl-4-pentene. Of these unsaturated oxiranes, particularly, 1,2-epoxy-3-butene is favorable in consideration of such as easy availability.

The amount of the aforementioned unsaturated oxirane as used is not smaller than 0.1 time by mol, favorably in the range of 0.5 to 1.5 times by mol, more favorably 1.0 to 1.2 times by mol, of the aforementioned unsaturated carboxylic acid. In case where the amount of the aforementioned unsaturated oxirane as used is smaller than 0.1 time by mol of the aforementioned unsaturated carboxylic acid, a hydroxyl group as formed by ring-opening addition of the unsaturated oxirane to the unsaturated carboxylic acid tends to react further with another unsaturated carboxylic acid to form an unsaturated carboxylic acid diester as a by-product. This unsaturated carboxylic acid diester causes gelation during polymerization because of having two unsaturated groups polymerizable to nearly the same extent as each other per molecule.

In the present invention, a catalyst is used for the reaction. Examples of this catalyst include at least one member selected from the group consisting of chromium compounds, manganese compounds, iron compounds, nickel compounds, zinc compounds, silver compounds, tin compounds, neodymium compounds, and lead compounds. In the present invention, of these catalysts, particularly, the chromium compounds, the manganese compounds, the nickel compounds, the silver compounds, the neodymium compounds, and the lead compounds are favorable, and the chromium compounds are the most favorable. The use of these compounds as catalysts can inhibit the rearrangement of the carbon-carbon unsaturated bond of the raw unsaturated oxirane.

The aforementioned chromium compounds are not especially limited, but examples thereof include chromium chloride, chromium bromide, chromium saturated-carboxylates (e.g. chromium acetate, chromium propionate, chromium 2-ethylhexanoate), chromium unsaturated-carboxylates (e.g. chromium acrylate, chromium methacrylate), chromium sulfate, chromium oxide, and chromium acetylacetonate.

The amount of the catalyst is not especially limited, but is usually in the range of 0.01 to 20 weight %, favorably 0.05 to 10 weight %, more favorably 0.1 to 5 weight %, of the aforementioned unsaturated carboxylic acid. In the case where the amount of the catalyst is smaller than 0.01 weight % of the aforementioned unsaturated carboxylic acid, the reaction rate tends to be very slow. On the other hand, in the case where the amount of the catalyst exceeds 20 weight %, there is no bad influence on the reaction, but there are economical disadvantages.

The reaction temperature may be adjusted into the range of 0 to 150° C., favorably 50 to 100° C. In the case where the reaction temperature is lower than 0° C., the reaction rate tends to be very slow. On the other hand, in the case where the reaction temperature is higher than 150° C., there are disadvantages in that many side reactions arise. Incidentally, it is not always necessary to carry out the reaction at a constant temperature, but the reaction temperature in the first half of the reaction can be different from that in the second half of the reaction.

The reaction pressure is not especially limited, but may be adjusted into the range of usually 0.098 to 9.8 MPa, favorably 0.098 to 1.96 MPa.

The reaction time depends upon such as the kind or amount of the catalyst as used and the reaction temperature, but is generally in the range of about 1 to about 24 hours.

The reaction is favorably carried out under an atmosphere of an inert gas such as nitrogen, argon, and helium, but is not limited thereto.

The reaction may be carried out either in or without a solvent, but is favorably carried out under a solvent reflux in consideration of effective removal of reaction heat. When the solvent is used, the concentration of the reaction mixture is usually favorably in the range of about 5 to about 90 weight %. In the case where the concentration is less than 5 weight %, the reaction rate is slow, and further there are economical disadvantages in that it is necessary to recover a large amount of solvent in order to isolate the aimed product. On the other hand, the concentration exceeds 90 weight %, the effect of dilution by the solvent is not displayed enough.

If the reaction solvent is inactive on the unsaturated carboxylic acid and the unsaturated oxirane, the reaction solvent is not especially limited, but examples thereof include: hydrocarbon solvents, such as hexane, cyclohexane, pentane, benzene, toluene, xylene, p-cymene, and mesitylene; halogenated hydrocarbon solvents, such as dichloromethane, dichloroethane, chloroform, carbon tetrachloride, and chlorobenzene; ether solvents, such as diethyl ether, dibutyl ether, tetrahydrofuran, dioxane, dioxolane, 1,2-dimethoxyethane, and diethylene glycol dimethyl ether; ketone solvents, such as acetone, methyl ethyl ketone, and methyl isobutyl ketone; amide solvents, such as N,N-dimethylformamide, N,N-dimethylacetamide, formamide, N-methylpyrrolidone, and 1,3-dimethyl-2-imidazolidone; sulfoxide or sulfone solvents, such as dimethyl sulfoxide and sulfolane; and further, acetonitrile, nitromethane, and hexamethylphosphoric triamide. These reaction solvents can be used either alone respectively or in combinations with each other.

When carrying out the reaction, a polymerization inhibitor can also be used in order to inhibit the polymerization of an unsaturated group of the unsaturated carboxylic acid or resultant reaction product. If the polymerization inhibitor is that which is commonly used for this purpose, the polymerization inhibitor is not especially limited, but examples thereof include hydroquinone, hydroquinone monomethyl ether, methylhydroquinone, p-benzoquinone, catechol, t-butylcatechol, cresol, 2,4-dimethyl-6-t-butylphenol, phenothiazine, and copper dibutyldithiocarbamate. When using the polymerization inhibitor, its amount may be in the range of usually 0.001 to 1 weight %, favorably 0.01 to 0.5 weight %, of the aforementioned unsaturated carboxylic acid. In addition, in order to further enhance the polymerization inhibition effect, oxygen can be used together with the polymerization inhibitor by introducing oxygen into the reaction system. In this case, oxygen may be used by diluting it with an inert gas, when the oxygen concentration may be adjusted to not less than 0.05 volume %, favorably not less than 0.1 volume %. In the case where the oxygen concentration is less than 0.05 volume %, there are disadvantages in that the polymerization inhibition effect is not displayed enough.

The method for adding the raw materials for the reaction is not especially limited, but may be determined fitly for such as the kinds of the raw materials, the reaction temperature, the charging ratio to the unsaturated carboxylic acid, and the heating or cooling ability of reactors. Examples of the above method include: a method in which the raw materials, the catalyst and, if necessary, the polymerization inhibitor are mixed together at the beginning of the reaction; and a method in which the reaction is carried out while adding one or more of the raw materials.

The reaction form is not especially limited, and the reaction can be carried out in a batch manner, a half-batch manner, or a continuous manner, but, for the purpose of enhancing the selectivity of the aimed unsaturated carboxylate (unsaturated oxirane-1-mol adduct), it is more favorable to carry out the reaction by successively adding the unsaturated oxirane to the reaction system than by adding the raw materials all at once.

The reaction product resultant from the aforementioned reaction may thereafter be purified. The method for this purification is not especially limited, but the purification can be carried out by conventional methods such as distillation, crystallization, and extractive separation, and particularly the distillation is favorable. As to the conditions for the distillation, for example, the distillation temperature is in the range of 30 to 200° C., favorably 50 to 150° C., and the distillation pressure is in the range of 0.01 to 15 kPa, favorably 0.05 to 5 kPa. Particularly in the case where the distillation temperature is high than 200° C., gelation easily occurs, therefore it is favorable that the distillation is carried out under conditions where the distillation pressure is depressed.

In the ring-opening addition reaction of the unsaturated oxirane to the unsaturated carboxylic acid, the molar number of the addition of the unsaturated oxirane in the resultant product varies with such as the charging ratios of the raw materials or the type of the catalyst, and it is usually difficult to control the molar number of the addition of the unsaturated oxirane to 1 mol. For example, when the amount of the unsaturated oxirane as used is not smaller than an equivalent mol to the unsaturated carboxylic acid, it is usual that a large amount of multiple-mol adducts such as 2-mol adduct and 3-mol adduct easily form as by-products due to further addition of the unsaturated oxirane. However, the aforementioned production process according to the present invention enables to obtain the aimed unsaturated carboxylate (1-mol adduct) so selectively as to suppress the total content of the 2-mol adduct and the 3-mol adduct in the resultant unsaturated carboxylate into the aforementioned range.

In the ring-opening addition reaction of the unsaturated oxirane to the unsaturated carboxylic acid, an aldehyde compound might form due to the rearrangement of the unsaturated oxirane itself, but the aforementioned production process according to the present invention can suppress the content of the aldehyde compound in the resultant unsaturated carboxylate to not more than 5 weight %, favorably not more than 3 weight %, more favorably not more than 2 weight %. In the case where the production ratio of the aldehyde compound is more than 5 weight %, there occur problems of such as odors and toxicity.

(Uses of Unsaturated Carboxylate):

The unsaturated carboxylate according to the present invention is favorably used for the radical-curable resin composition according to the present invention. Namely, the radical-curable resin composition according to the present invention comprises a radical-curable resin, and further comprises at least the aforementioned unsaturated carboxylate according to the present invention as a reactive diluent and thereby displays not only excellent curability, but also excellent adhesion to substrates.

The aforementioned radical-curable resin, which is contained in the radical-curable resin composition according to the present invention, has no especial limitation if it is a radical-curable type resin which is cured by radical polymerization in the presence of radical generators such as curing agents or under irradiation with radiations such as ultraviolet rays, electron beams, and excimer lasers. Examples of such a radical-curable resin include: resins comprising reactive diluents and radical-curable polymers such as unsaturated polyesters, epoxy (meth)acrylates, urethane (meth)acrylates, polyester (meth)acrylates, and (meth) acrylic polymers; resins comprising (meth)acrylic syrup containing reactive diluents; and further resins comprising reactive diluents and polymers having no radical curability such as saturated polyesters and poly(methyl (meth) acrylate). These radical-curable resins may be used either alone respectively or in combinations with each other.

In the aforementioned radical-curable resin, the content of each of the aforementioned radical-curable polymers (which compose the radical-curable resin), such as unsaturated polyesters, epoxy (meth)acrylates, urethane (meth)acrylates, polyester (meth)acrylates, and (meth)acrylic polymers, is not especially limited, but is favorably in the range of 1 to 99 weight %, more favorably 5 to 95 weight %, still more favorably 10 to 90 weight %, of the radical-curable resin.

The content of the aforementioned unsaturated carboxylate, which is indispensable as the reactive diluent, in the radical-curable resin is not especially limited, but is favorably in the range of 1 to 99 weight %, more favorably 5 to 95 weight %, of the radical-curable resin.

Besides the aforementioned unsaturated carboxylate according to the present invention, other radical-polymerizable monomers may further be contained as the reactive diluent. Examples of such other radical-polymerizable monomers include: styrenic monomers such as styrene, vinyltoluene, p-t-butylstyrene, α-methylstyrene, p-chlorostyrene, p-methylstyrene, p-chloromethylstyrene, and divinylbenzene; (meth)acrylic acid and (meth)acrylate esters such as methyl (meth)acrylate, ethyl (meth)acrylate, cyclohexyl (meth)acrylate, hydroxyethyl (meth)acrylate, methoxyethoxyethyl (meth)acrylate, ethoxyethoxyethyl (meth)acrylate, phenoxyethyl (meth)acrylate, 2-hydroxyethyl (meth)acrylate, 2-hydroxypropyl (meth) acrylate, allyl (meth)acrylate, ethylene glycol di(meth) acrylate, diethylene glycol di(meth)acrylate, triethylene glycol di(meth)acrylate, and trimethylolpropane tri(meth) acrylate; allyl ester monomers such as diallyl phthalate and diallyl isophthalate. These radical-polymerizable monomers may be used either alone respectively or in combinations with each other. Incidentally, when these radical-polymerizable monomers are further contained as the reactive diluent, their total content in the radical-curable resin is not especially limited, but is favorably in the range of 1 to 99 weight %, more favorably 5 to 95 weight %, of the radical-curable resin.

The radical-curable resin composition according to the present invention is obtainable by adding the below-mentioned various additives to the aforementioned radical-curable resin, if necessary. The content of the aforementioned radical-curable resin in the radical-curable resin composition is not especially limited, but is usually in the range of 5 to 100 weight %, favorably 5 to 99.9 weight %, more favorably 5 to 99 weight %, still more favorably 5 to 90 weight %, of the radical-curable resin composition.

The method for curing the radical-curable resin composition according to the present invention is not especially limited. For example, the composition may be cured by irradiating it with radiations such as ultraviolet rays, electron beams, and excimer lasers or by adding radical generators such as curing agents to the composition.

In the case where the radical-curable resin composition according to the present invention is cured by the irradiation with radiations, a photopolymerization initiator besides the aforementioned radical-curable resin may further be contained in the composition. The addition of the photopolymerization initiator to the radical-curable resin composition according to the present invention makes it a photosensitive resin composition which is one of preferred embodiments of the present invention.

As to the aforementioned photopolymerization initiator, for example, conventional ones such as benzoins, acetophenones, thioxanthones, ketals, benzophenones, and 2,4,6-trimethylbenzoyldiphenylphosphine oxide are available. Specifically, examples of the benzoins include benzoin ethyl ether, benzoin butyl ether, and benzoin isopropyl ether. Examples of the acetophenones include acetophenone, 2,2-dimethoxy-2-phenylacetophenone, 2,2-diethoxy-2-phenylacetophenone, 1,1-dichloroacetophenone, 1-hydroxycyclohexyl phenyl ketone, 2-methyl-1-[4-(methylthio)phenyl]-2-morpholinopropan-1-one, and N,N-dimethylaminoacetophenone. Examples of the thioxanthones include 2,4-diethylthioxanthone, 2-chlorothioxanthone, and 2-isopropylthioxanthone. Examples of the ketals include benzyl dimethyl ketal and acetophenone dimethyl ketal. Examples of the benzophenones include benzophenone, methylbenzophenone, 4,4'-bisdiethylaminobenzophenone, and 4-benzoyl-4'methyldiphenyl sulfide. These photopolymerization initiators may be used either alone respectively or in combinations with each other.

The amount of the aforementioned photopolymerization initiator as used is not especially limited, but it is desirable to use it in the range of 0.1 to 15 weight %, favorably 1 to 10 weight %, of the radical-curable resin.

In the case where the radical-curable resin composition according to the present invention is cured by the irradiation with radiations, the below-mentioned curing agents (so-called heat-radical-curable initiators such as peroxides and azo compounds) may be used jointly with the aforementioned photopolymerization initiator.

In the case where the radical-curable resin composition according to the present invention is cured by the addition of the radical generators such as curing agents thereto, a conventional curing agent besides the aforementioned radical-curable resin may further be contained in the composition.

Examples of the aforementioned curing agent include organic peroxides and azo compounds. Specifically, examples of the organic peroxide include: ketone peroxides such as methyl ethyl ketone peroxide and acetylacetone peroxide; hydroperoxides such as cumene hydroperoxide; diacyl peroxides such as benzoyl peroxide; dialkyl peroxides such as dicumyl peroxide and t-butylcumyl peroxide; alkyl peresters such as 1,1,3,3-tetramethylbutyl peroxy-2-ethylhexanoate, t-butyl peroxy-2-ethylhexanoate, and t-butyl peroxyhexanoate; and peroxycarbonates such as bis (4-t-butylcyclohexyl) peroxycarbonate. In addition, examples of the azo compound include 2,2'-azobisisobutyronitrile and 2,2'-azobis-2-methylbutyronitrile. These curing agents may be used either alone respectively or in combinations with each other.

The amount of the aforementioned curing agent as used may fitly be set for the gelation time to be fit for uses and is therefore not especially limited, but it is desirable to use it in the range of 0.1 to 10 weight % of the radical-curable resin.

In the case where the radical-curable resin composition according to the present invention is cured by the addition of the radical generators such as curing agents thereto, a conventional curing promotor may be used jointly with the aforementioned curing agent. The curing promotor has no especial limitation if it is a compound having a redox function. Specific examples thereof include: metal soaps such as cobalt octylate and manganese octylate; metal chelate compounds such as cobalt acetylacetonate and vanadium acetylacetonate; amine compounds such as dimethylaniline and dimethyltoluidine; ethyl acetoacetate; and acetylacetone. These curing promotors may be used either alone respectively or in combinations with each other.

The amount of the aforementioned curing promotor as used may fitly be set for the gelation time to be fit for uses according to such as the constitution of the radical-curable resin composition and the type of the curing agent or curing promotor as used, and is therefore not especially limited, but it is desirable to use the curing promotor in the range of 0.1 to 10 weight % of the radical-curable resin.

The aforementioned curing agent or curing promotor may be beforehand contained in the aforementioned radical-curable resin composition or may be mixed into the composition just before its curing. In addition, when the radical-curable resin composition is cured with these curing agent and curing promotor, the curing temperature is different according to the types and addition amounts of these curing agent and curing promotor or other conditions and is therefore not especially limited, but is favorably in the range of −30 to 150° C., more favorably −30 to 80° C., still more favorably −30 to 50° C.

The radical-curable resin composition according to the present invention may further comprise conventional additives, such as shrinkage-reducing agents, colorants, paraffin waxes, organometallic soaps, silane coupling agents, thixotropifiers, thixotropifying assistants, thickeners, plasticizers, ultraviolet absorbents, antioxidants, flame retardants, stabilizers, fillers (e.g. calcium carbonate, aluminum hydroxide), and reinforcing fibers (e.g. glass fibers, carbon fibers), according to uses of the composition within the range not damaging the effects of the present invention.

The radical-curable resin composition according to the present invention has the hydrophilicity and the adhesion to various substrates along with the curability and the hardness of the resultant cured product, and is therefore usable favorably for various uses such as adhesives, pressure sensitive adhesives, dental materials, optical members, information-recording materials, optical fiber materials, resist materials, sealants, printing inks, paints, casting materials, face plates, WPC, coating materials, waterproofing materials, lining materials, civil engineering and building materials, putty, repairing materials, floor materials, gel coats for various uses (e.g. gel coats for paving materials, overcoatings), molding materials (e.g. hand-lay-up, spray-up, abstraction molding, filament winding, SMC, BMC), and sheets.

The unsaturated carboxylate according to the present invention can be either homopolymerized or copolymerized with another polymerizable unsaturated monomer. An unsaturated carboxylate polymer, which is obtained by a process including the step of polymerizing a monomer component comprising at least the unsaturated carboxylate, has both the unsaturated group and the hydroxyl group in side chains and is therefore useful for uses such as resin-molded structures, paints, pressure sensitive adhesives, adhesives, resin additives, films, and active-energy-curable resins.

Examples of the above other polymerizable unsaturated monomer, usable as the above monomer component, include: (meth)acrylate esters synthesized by esterification of (meth)acrylic acid with C1 to C18 alcohols, such as methyl (meth)acrylate, ethyl (meth)acrylate, butyl (meth) acrylate, and cyclohexyl (meth)acrylate; hydroxyl-group-containing monomers such as hydroxyethyl (meth)acrylate and hydroxypropyl (meth)acrylate; (meth)acrylamide and derivatives therefrom such as N-monomethyl(meth) acrylamide, N-monoethyl(meth)acrylamide, and N,N-dimethyl(meth)acrylamide; basic monomers such as dimethylaminoethyl(meth)acrylate, dimethylaminoethyl (meth)acrylamide, vinylpyridine, and vinylimidazole; cyclic vinylamides such as vinylpyrrolidone, vinyloxazolidone, and vinylcaprolactam; carboxyl-group-containing monomers, such as (meth)acrylic acid, itaconic acid, maleic acid, and fumaric acid, and their neutralized products such as sodium (meth)acrylate; unsaturated acid anhydrides such as maleic anhydride and itaconic anhydride; 2-sulfoethyl (meth)acrylate and derivatives therefrom; vinylsulfonic acid and derivatives therefrom; vinyl esters such as vinyl acetate, vinyl propionate, vinyl pivalate, and vinyl stearate; vinyl ethers such as methyl vinyl ether, ethyl vinyl ether, and butyl vinyl ether; and olefins such as ethylene, propylene, octene, and butadiene. These may be used either alone respectively or in combinations with each other.

In the case where the aforementioned polymerizable unsaturated monomer is used, the ratio of the aforementioned unsaturated carboxylate to the polymerizable unsaturated monomer is favorably in the range of (unsaturated carboxylate)/(polymerizable unsaturated monomer)=(0.1 to 50 mol %)/(50 to 99.9 mol %), more favorably (0.5 to 30 mol %)/(70 to 99.5 mol %), still more favorably (1.0 to 20 mol %)/(80 to 99.0 mol %).

When the aforementioned monomer component is polymerized, the polymerization method is not especially limited. For example, conventional ones such as bulk polymerization, solution polymerization, suspension polymerization, and emulsion polymerization are usable. In addition, the polymerization may involve the use of conventional solvents and, in such cases, the concentration of the monomer component is favorably in the range of 1 to 99 weight %, more favorably 10 to 90 weight %, still more favorably 20 to 80 weight %.

In addition, the polymerization can involve the use of conventional polymerization initiators, and the amount thereof as used is favorably in the range of 0.001 to 10 weight %, more favorably 0.01 to 5 weight %, still more favorably 0.1 to 3 weight %, of the monomer component. In the case where the amount of the polymerization initiator is smaller than 0.001 weight %, the polymerization reaction rate is very slow. On the other hand, in the case where the amount of the polymerization initiator is larger than 10 weight %, many side reactions occur. Therefore, both cases are unfavorable. Incidentally, if necessary, the polymerization may involve the use of: chain transfer agents such as laurylmercaptan and mercaptoethanol; or adjusting agents.

The temperature for the aforementioned polymerization is favorably in the range of 0 to 300° C., more favorably 10 to 200° C., still more favorably 25 to 150° C. In the case where the polymerization temperature is lower than 0° C., the polymerization reaction rate is very slow. On the other hand, in the case where the polymerization temperature is higher than 300° C., many side reactions occur. Therefore, both cases are unfavorable. In addition, the polymerization reaction is favorably carried out under an atmosphere of an inert gas such as nitrogen, argon, and helium, but is not limited thereto.

(Effects and Advantages of the Invention):

The novel unsaturated carboxylate, according to the present invention, has both an unsaturated group and a hydroxyl group, and is applicable to a wide range of crosslinking processes, and has moderate polymerizability. In addition, the production process for an unsaturated carboxylate, according to the present invention, causes no rearrangement of the carbon-carbon unsaturated bond of the raw unsaturated oxirane, and further, enables to obtain the unsaturated oxirane-1-mol adduct with good efficiency. In addition, the radical-curable resin composition, according to the present invention, displays not only excellent curability, but also excellent adhesion to substrates. In addition, the unsaturated carboxylate polymer, according to the present invention, has both the unsaturated group and the hydroxyl group, and is widely utilizable for various uses.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to the examples of some preferred embodiments.

The analyses by gas chromatography of the resultant reaction product and the purified unsaturated carboxylate were carried out under the following conditions:

Instrument: "Gas Chromatograph GC-15A" produced by Shimadzu Corporation

Column: "Nonpolar Capillary Column SPB-1" produced by SPELCO

Carrier gas: helium

Detector: hydrogen flame ionization detector (FID)

EXAMPLE 1

A flask, as equipped with a stirrer, a reflux condenser, a thermometer, a dropping funnel, and a nitrogen-gas-introducing tube, was charged with 50.5 g (0.7 mol) of acrylic acid, 1.5 g of chromium acetate (3 weight % of acrylic acid), and 0.13 g of hydroquinone monomethyl ether (0.3 weight % of acrylic acid). Then, 54.0 g (0.77 mol) of 1,2-epoxy-3-butene was dropwise added over a period of 2 hours while maintaining the temperature at 80° C. under a nitrogen gas stream. After the reaction was carried out at this temperature for another 2 hours, the resultant reaction product was got out and then analyzed by gas chromatography. As a result, the conversion of acrylic acid was 99.5%, and the conversion of 1,2-epoxy-3-butene was 97.7%. In addition, the resultant reaction product contained a 1,4-adduct and crotonaldehyde in the ratios of 0.6 weight % and 0.5 weight % respectively.

In addition, as a result of the above gas chromatographic analysis, the production ratio of a 1-mol adduct was 85.8 mol % of the converted acrylic acid, and the production ratios of 2-mol and 3-mol adducts as formed by further addition of 1,2-epoxy-3-butene were 10.2 mol % and 3.0 mol %, respectively, of the converted acrylic acid, and 4-mol or more multiple-mol adducts were not detected. From these results, (1-mol adduct)/{(2-mol adduct)+(3-mol adduct)} (molar ratio) was found 6.5.

Figure 1:
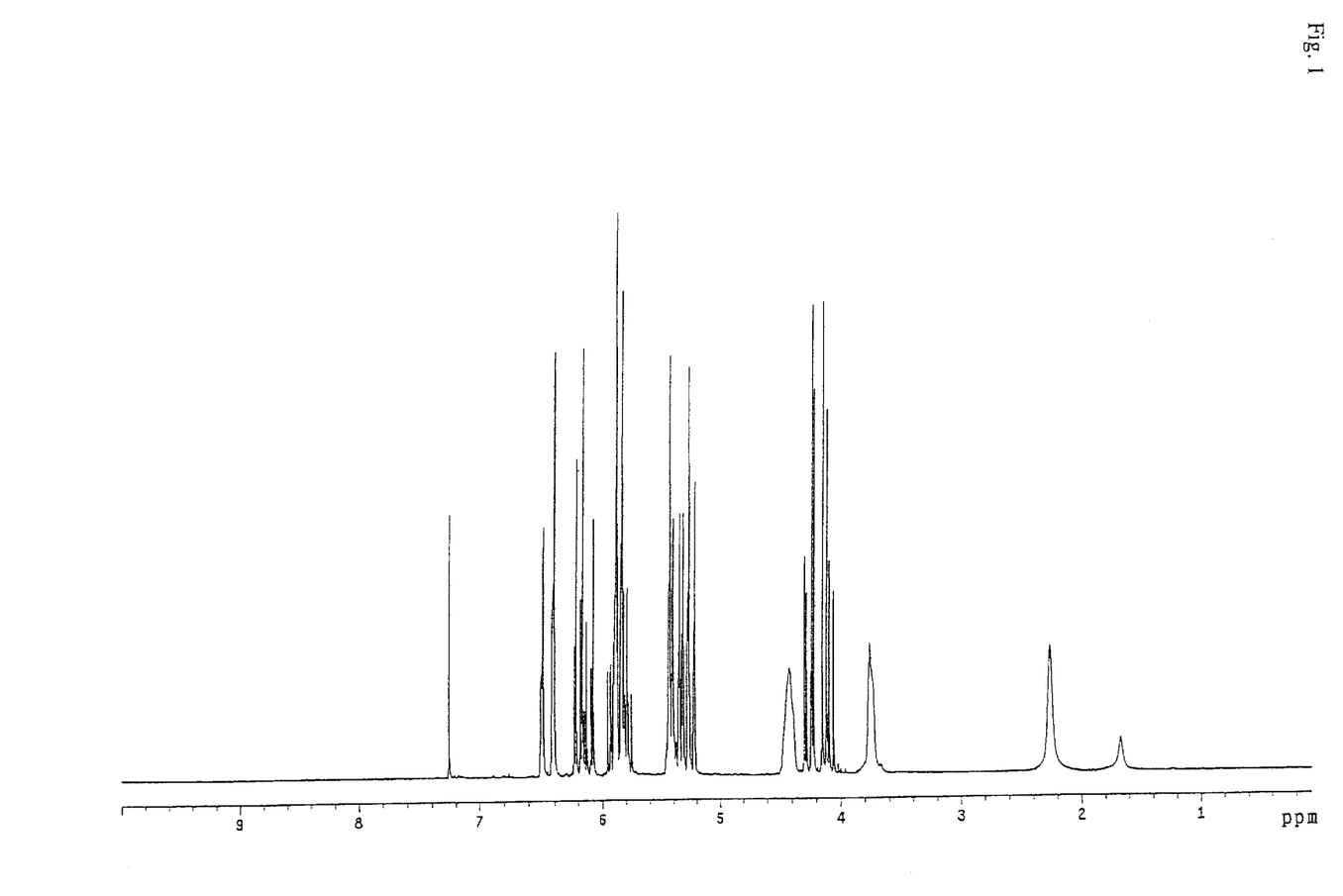
FIG. 1 is a ¹H-NMR spectrochart of the unsaturated carboxylate as obtained in Example 1.
Figure 2:
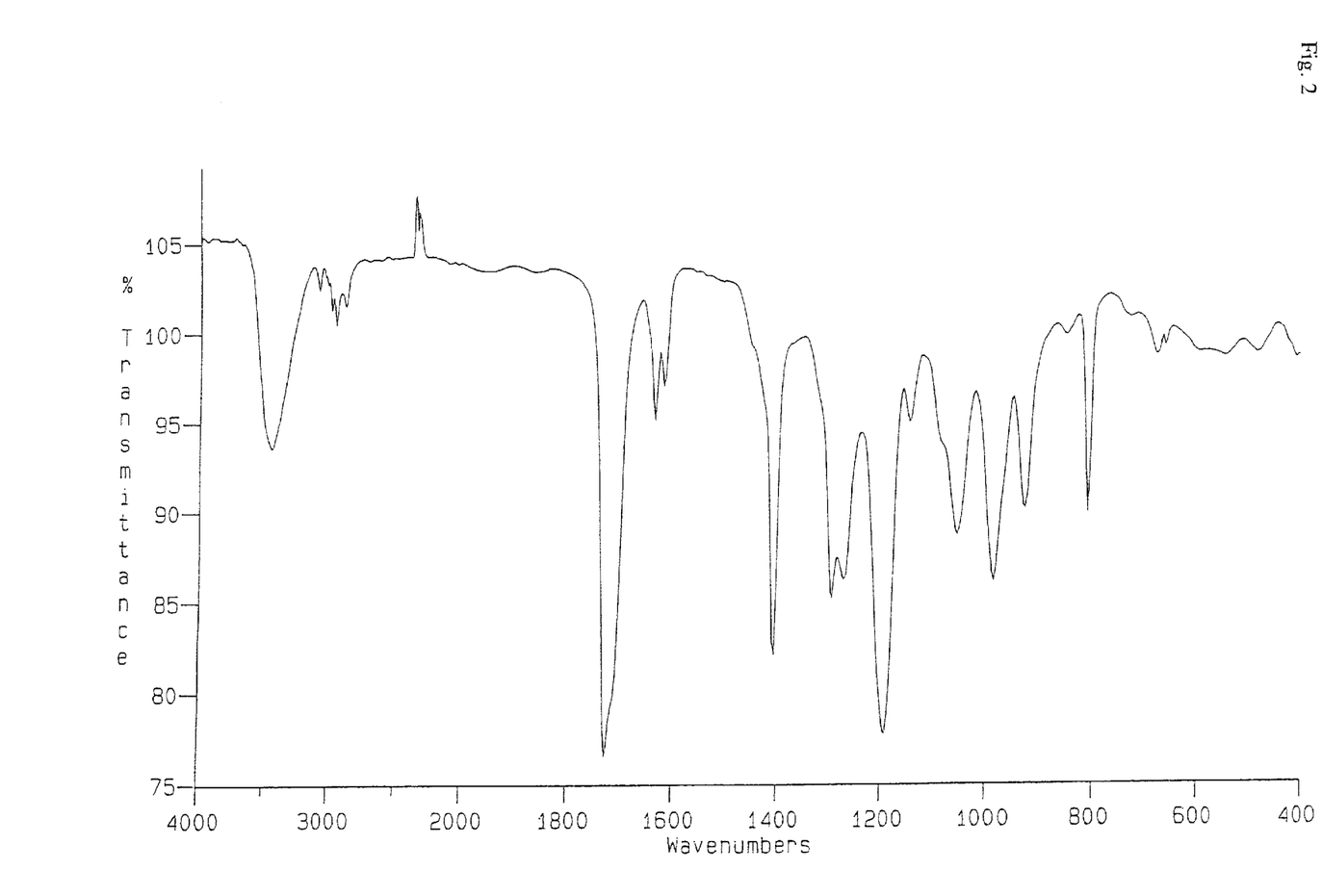
FIG. 2 is an infrared absorption spectrochart of the unsaturated carboxylate as obtained in Example 1.

The reaction product was distilled under reduced pressure, whereby a mixture of 2-hydroxy-1-vinylethyl acrylate (hereinafter, referred to as "compound A") and 2-hydroxy-2-vinylethyl acrylate (hereinafter, referred to as "compound B") was obtained as a colorless transparent liquid of the weight of 83.6 g (yield based on acrylic acid: 84%, boiling point: 92 to 93° C./0.8 kPa). As a result of $^1$H-NMR analysis, the ratio of compound A to compound B was compound A/compound B=70/30 (molar ratio). A $^1$H-NMR spectrochart and an infrared absorption spectrochart (by a liquid membrane method) of the mixture of compounds A and B are shown in FIGS. 1 and 2 respectively.

<$^1$H-NMR Spectrum>

The $^1$H-NMR spectrum was measured at room temperature in a deuterium chroloform solvent using tetramethylsilane as the internal standard substance. Incidentally, hereinafter, X represents a vinyl group.

δ 1.66 ppm (0.3H); proton of hydroxyl group in compound B

δ 2.24 ppm (0.7H); proton of hydroxyl group in compound A

δ 3.77 ppm (0.6H); protons of methylene group of —CH$_2$—CHX—OH in compound B

δ 4.06 to 4.31 ppm (1.4H); protons of methylene group of —CHX—CH$_2$—OH in compound A δ 4.43 ppm (0.7H); proton of methyne group of —CHX—CH$_2$—OH in compound A δ 5.23 to 5.47 ppm (2.3H); protons of CH$_2$ of vinyl group and proton of methyne group of —CH$_2$—CHX—OH in compound B δ 5.76 to 5.97 ppm (2.0H); one of protons of CH$_2$ that is an end of double bond in acryl group and proton of CH of vinyl group δ 6.09 to 6.25 ppm (1.0H); proton of CH that is an end of double bond in acryl group δ 6.41 to 6.52 ppm (1.0H); the other proton of CH$_2$ that is an end of double bond in acryl group <Infrared Absorption Spectrum (by Liquid Membrane Method)>
3447 cm$^{-1}$; O—H stretching vibration
1728 cm$^{-1}$; C=O stretching vibration
1636 cm$^{-1}$; C=C stretching vibration
1619 cm$^{-1}$; C=C stretching vibration
1194 cm$^{-1}$; C=O stretching vibration

EXAMPLE 2

A flask, as equipped with a stirrer, a reflux condenser, a thermometer, a dropping funnel, and a nitrogen-gas-introducing tube, was charged with 361.7 g (4.2 mol) of methacrylic acid, 3.6 g of chromium acetate (1 weight % of methacrylic acid), and 0.18 g of hydroquinone monomethyl ether (0.05 weight % of methacrylic acid). Then, 323.8 g (4.62 mol) of 1,2-epoxy-3-butene was dropwise added over a period of 3 hours while maintaining the temperature at 90° C. under a nitrogen gas stream. After the reaction was carried out at this temperature for another 1 hour, the resultant reaction product was got out and then analyzed by gas chromatography. As a result, the conversion of methacrylic acid was 99.8%, and the conversion of 1,2-epoxy-3-butene was 95.5%. In addition, the resultant reaction product contained a 1,4-adduct and crotonaldehyde in the ratios of 0.3 weight % and 0.2 weight % respectively.

In addition, as a result of the above gas chromatographic analysis, the production ratio of a 1-mol adduct was 95.1 mol % of the converted methacrylic acid, and the production ratios of 2-mol and 3-mol adducts as formed by further addition of 1,2-epoxy-3-butene were 3.9 mol % and 0.3 mol %, respectively, of the converted methacrylic acid, and 4-mol or more multiple-mol adducts were not detected. From these results, (1-mol adduct)/{(2-mol adduct)+(3-mol adduct)} (molar ratio) was found 22.6.

Figure 3:
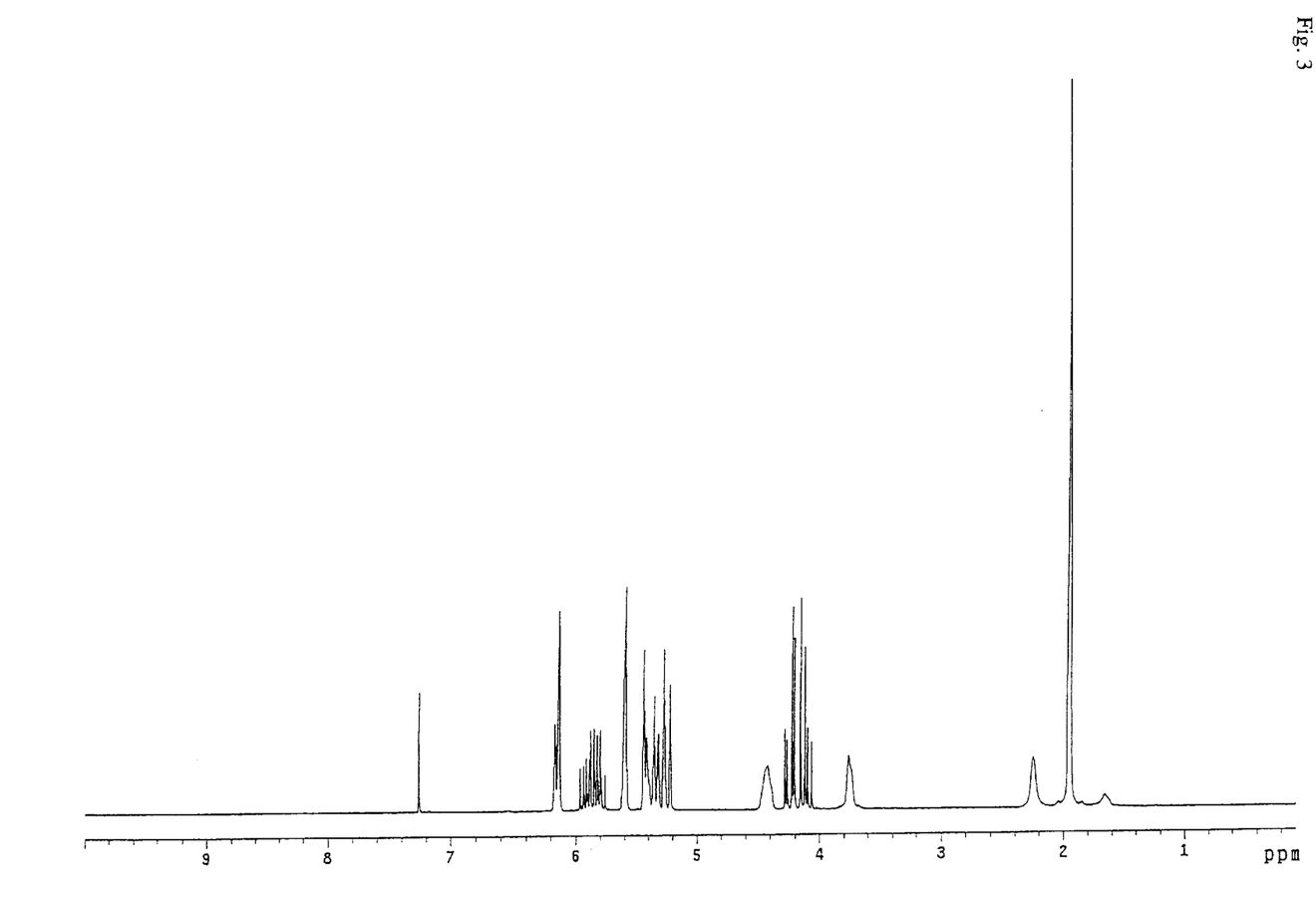
FIG. 3 is a ¹H-NMR spectrochart of the unsaturated carboxylate as obtained in Example 2.
Figure 4:
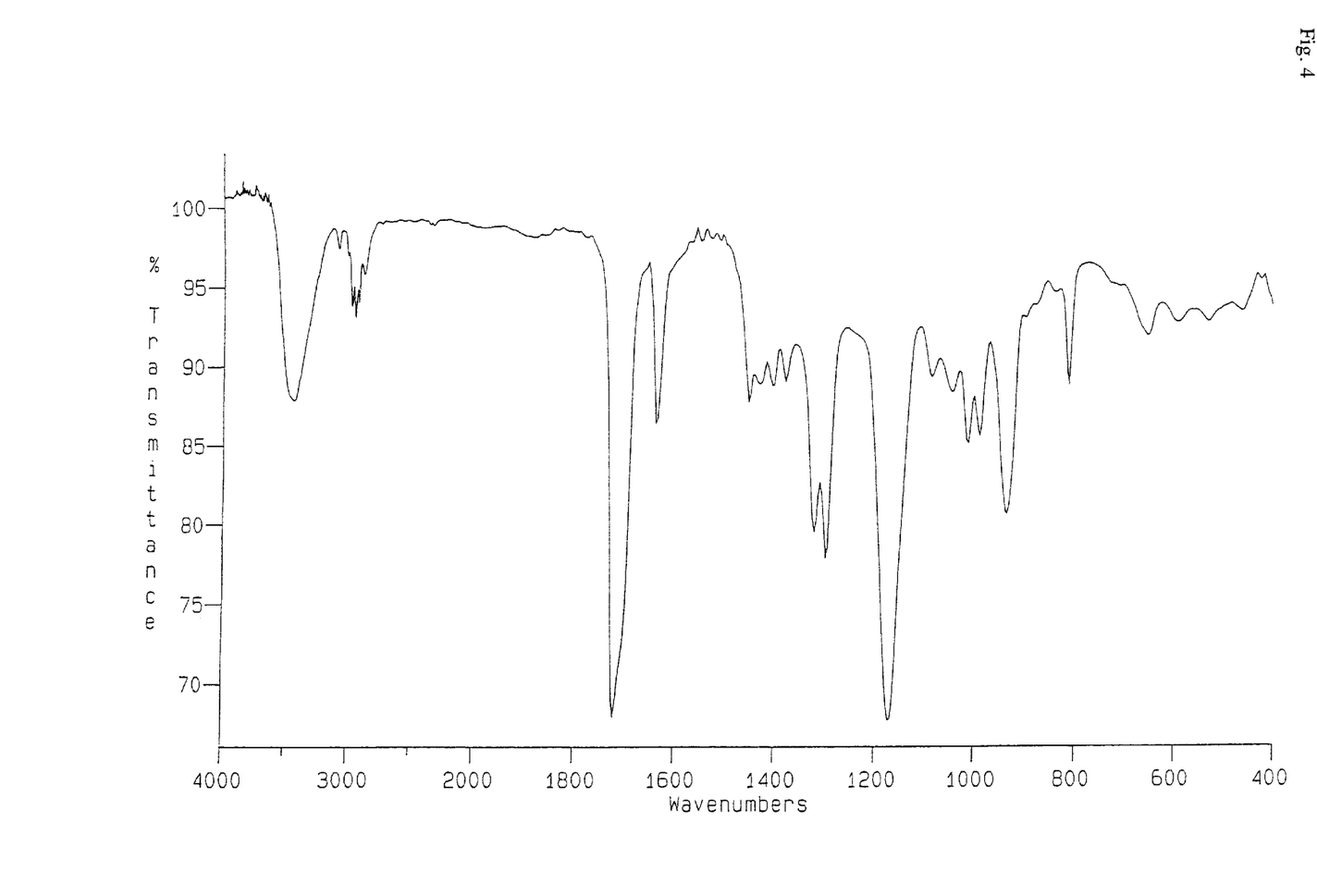
FIG. 4 is an infrared absorption spectrochart of the unsaturated carboxylate as obtained in Example 2.

The reaction product was distilled under reduced pressure, whereby a mixture of 2-hydroxy-1-vinylethyl methacrylate (hereinafter, referred to as "compound C") and 2-hydroxy-2-vinylethyl methacrylate (hereinafter, referred to as "compound D") was obtained as a colorless transparent liquid of the weight of 613.0 g (yield based on methacrylic acid: 93%, boiling point: 96 to 97° C./0.67 kPa). As a result of $^1$H-NMR analysis, the ratio of compound C to compound D was compound C/compound D=70/30 (molar ratio). A $^1$H-NMR spectrochart and an infrared absorption spectrochart (by a liquid membrane method) of the mixture of compounds C and D are shown in FIGS. 3 and 4 respectively.

<$^1$H-NMR Spectrum>
The $^1$H-NMR spectrum was measured at room temperature in a deuterium chroloform solvent using tetramethylsilane as the internal standard substance. Incidentally, hereinafter, X represents a vinyl group.

δ 1.67 ppm (0.3H); proton of hydroxyl group in compound D

δ 1.95 ppm (3.0H); protons of CH$_3$ of methacryl group

δ 2.26 ppm (0.7H); proton of hydroxyl group in compound C

δ 3.76 ppm (0.6H); protons of methylene group of —CH$_2$—CHX—OH in compound D

δ 4.06 to 4.28 ppm (1.4H); protons of methylene group of —CHX—CH$_2$—OH in compound C δ 4.42 ppm (0.7H); proton of methyne group of —CHX—CH$_2$—OH in compound C δ 5.21 to 5.45 ppm (2.3H); protons of CH$_2$ of vinyl group and proton of methyne group of —CH$_2$—CHX—OH in compound D δ 5.60 ppm (1.0H); one of protons of CH$_2$ that is an end of double bond in methacryl group δ 5.76 to 5.97 ppm (1.0H); proton of CH of vinyl group δ 6.13 ppm (1.0H); the other proton of CH$_2$ that is an end of double bond in methacryl group <Infrared Absorption Spectrum (by Liquid Membrane Method)>
3440 cm$^{-1}$; O—H stretching vibration
1721 cm$^{-1}$; C=O stretching vibration
1638 cm$^{-1}$; C=C stretching vibration
1171 cm$^{-1}$; C—O stretching vibration

EXAMPLE 3

A flask, as equipped with a stirrer, a reflux condenser, a thermometer, a dropping funnel, and a nitrogen-gas-introducing tube, was charged with 51.7 g (0.6 mol) of methacrylic acid, 0.5 g of chromium acetate (1 weight % of methacrylic acid), and 0.026 g of hydroquinone monomethyl ether (0.05 weight % of methacrylic acid). Then, 84.1 g (1.2 mol) of 1,2-epoxy-3-butene was dropwise added over a period of 3 hours while maintaining the temperature at 90° C. under a nitrogen gas stream. After the reaction was carried out at this temperature for another 1 hour, the resultant reaction product was got out and then analyzed by gas chromatography. As a result, the conversion of methacrylic acid was 99.9 %, and the conversion of 1,2-epoxy-3-butene was 56.1%. The yield of the aimed mixture of the compounds C and D was 91.0% (based on methacrylic acid). In addition, the resultant reaction product contained a 1,4-adduct and crotonaldehyde in the ratios of 0.4 weight % and 0.2 weight % respectively.

In addition, as a result of the above gas chromatographic analysis, the production ratio of a 1-mol adduct was 91.0 mol % of the converted methacrylic acid, and the production ratios of 2-mol and 3-mol adducts as formed by further addition of 1,2-epoxy-3-butene were 6.8 mol % and 0.7 mol %, respectively, of the converted methacrylic acid, and 4-mol or more multiple-mol adducts were not detected. From these results, (1-mol adduct)/{(2-mol adduct)+(3-mol adduct)} (molar ratio) was found 12.1.

EXAMPLE 4

A flask, as equipped with a stirrer, a reflux condenser, a thermometer, and a nitrogen-gas-introducing tube, was charged with 8.61 g (0.1 mol) of methacrylic acid, 8.41 g (0.12 mol) of 1,2-epoxy-3-butene, 0.43 g of manganese acetate tetrahydrate (5 weight % of methacrylic acid), and 0.004 g of hydroquinone monomethyl ether (0.05 weight % of methacrylic acid). Then, the resultant mixture was allowed to react for 3 hours while maintaining the temperature at 70° C. under a nitrogen gas stream.

Table 1 shows the results of the analysis of the resultant reaction product by gas chromatography (conversions of methacrylic acid and 1,2-epoxy-3-butene; yield (based on methacrylic acid) of the aimed mixture of compounds C and D; (1-mol adduct)/{(2-mol adduct)+(3-mol adduct)} (molar ratio); and contents of 1,4-adduct and crotonaldehyde).

EXAMPLES 5 TO 11

Reactions were carried out under the same conditions and by the same procedure as of Example 4 except that the manganese acetate tetrahydrate was replaced with catalysts (all their amounts were 5 weight % of methacrylic acid) as listed in Table 1.

Table 1 further shows the results of analyses of the resultant reaction products by gas chromatography (conversions of methacrylic acid and 1,2-epoxy-3-butene; yield (based on methacrylic acid) of the aimed mixture of compounds C and D; (1-mol adduct)/{(2-mol adduct)+(3-mol adduct)}(molar ratio); and contents of 1,4-adduct and crotonaldehyde).

TABLE 1

| | | Conversion (%) of methacrylic acid | Conversion (%) of 1,2-epoxy-3-butene | Yield (%) of mixture of compounds C and D | Content (wt %) of 1,4-adduct | Content (wt %) of crotonaldehyde | (1-mol adduct)/{(2-mol adduct) + (3-mol adduct)} (molar ratio) |
|---|---|---|---|---|---|---|---|
| Example 4 | Manganese acetate tetrahydrate | 68.4 | 79.8 | 50.5 | 0.4 | N.D. | 3.4 |
| Example 5 | Iron citrate hydrate | 74.2 | 72.5 | 38.7 | 0.5 | 0.3 | 1.4 |
| Example 6 | Nickel acetate tetrahydrate | 63.0 | 77.2 | 45.6 | 0.3 | 0.1 | 3.1 |
| Example 7 | Zinc acetate dihydrate | 81.5 | 78.7 | 43.6 | 1.1 | 0.3 | 1.5 |
| Example 8 | Silver acetate | 58.2 | 67.8 | 41.6 | 0.3 | 0.1 | 2.7 |
| Example 9 | Tin acetate | 72.0 | 77.8 | 36.1 | 0.1 | 0.2 | 1.3 |
| Example 10 | Neodymium acetate monohydrate | 68.6 | 78.3 | 50.9 | 0.4 | 0.1 | 3.5 |
| Example 11 | Lead acetate trihydrate | 58.8 | 69.7 | 43.9 | 0.3 | 0.1 | 3.8 |

EXAMPLE 12

A reaction product as not yet distilled under reduced pressure was produced in the same way as of Example 1, and then 350 g of ethyl acetate was added to this reaction product, and the resultant mixture was washed with 400 g of pure water twice. Next, low boiling point volatiles were removed from the resultant ethyl acetate solution with an evaporator to obtain a purified unsaturated carboxylate.

The resultant purified unsaturated carboxylate was analyzed by gas chromatography. As a result, the content of a 1-mol adduct was 92.0 mol %, and the contents of 2-mol and 3-mol adducts as formed by further addition of 1,2-epoxy-3-butene were 6.0 mol % and 0.5 mol % respectively, and 4-mol or more multiple-mol adducts were not detected. From these results, (1-mol adduct)/{(2-mol adduct)+(3-mol adduct)} (molar ratio) was found 14.1.

EXAMPLE 13

A reaction product as not yet distilled under reduced pressure was produced in the same way as of Example 2, and then 350 g of ethyl acetate was added to this reaction product, and the resultant mixture was washed with 400 g of pure water twice. Next, low boiling point volatiles were removed from the resultant ethyl acetate solution with an evaporator to obtain a purified unsaturated carboxylate.

The resultant purified unsaturated carboxylate was analyzed by gas chromatography. As a result, the content of a 1-mol adduct was 96.0 mol %, and the contents of 2-mol and 3-mol adducts as formed by further addition of 1,2-epoxy-3-butene were 3.0 mol % and 0.5 mol % respectively, and 4-mol or more multiple-mol adducts were not detected. From these results, (1-mol adduct)/{(2-mol adduct)+(3-mol adduct)} (molar ratio) was found 27.4.

COMPARATIVE EXAMPLE 1

A reaction was carried out under the same conditions and by the same procedure as of Example 2 except that the chromium acetate was replaced with boron trifluoride-diethyl ether complex (1 weight % of methacrylic acid). However, the reaction mixture in the flask solidified immediately after the initiation of the dropwise addition of 1,2-epoxy-3-butene, therefore it was impossible to continue the reaction.

COMPARATIVE EXAMPLE 2

A reaction was carried out under the same conditions and by the same procedure as of Example 2 except that the chromium acetate was replaced with boron trifluoride-diethyl ether complex (1 weight % of methacrylic acid), and that the reaction temperature was adjusted into the range of 50 to 60° C. The resultant reaction product was got out and then analyzed by gas chromatography. As a result, the conversion of methacrylic acid was 31.2%, and the conversion of 1,2-epoxy-3-butene was 68.2%. The yield of the aimed mixture of the compounds C and D was 7.2% (based on methacrylic acid). In addition, the resultant reaction product contained a 1,4-adduct and crotonaldehyde in the ratios of 1.2 weight % and 1.0 weight % respectively.

In addition, as a result of the above gas chromatographic analysis, the production ratio of a 1-mol adduct was 23.1 mol % of the converted methacrylic acid, and the production ratios of 2-mol and 3-mol adducts as formed by further addition of 1,2-epoxy-3-butene were 23.1 mol % and 12.5 mol %, respectively, of the converted methacrylic acid, and the production ratios of 4-mol and 5-mol adducts were 10.5 mol % and 7.8 mol %, respectively, of the converted methacrylic acid, and 6-mol or more multiple-mol adducts were not detected. From these results, (1-mol adduct)/{(2-mol adduct)+(3-mol adduct)} (molar ratio) was found 0.7.

COMPARATIVE EXAMPLE 3

A reaction was carried out under the same conditions and by the same procedure as of Example 1 except that the chromium acetate was replaced with boron trifluoride-diethyl ether complex (3 weight % of acrylic acid), and that the reaction temperature was adjusted to 50° C. To the resultant reaction product, 350 g of ethyl acetate was added, and the resultant mixture was washed with 400 g of pure water twice. Next, low boiling point volatiles were removed from the resultant ethyl acetate solution with an evaporator to obtain a purified unsaturated carboxylate.

The resultant purified unsaturated carboxylate was analyzed by gas chromatography. As a result, the content of a 1-mol adduct was 22.0 mol %, and the contents of 2-mol and 3-mol adducts as formed by further addition of 1,2-epoxy-3-butene were 23.1 mol % and 12.5 mol % respectively, and the contents of 4-mol and 5-mol adducts were 10.5 mol % and 7.8 mol % respectively, and 6-mol or more multiple-mol adducts were not detected. From these results, (1-mol adduct)/{(2-mol adduct)+(3-mol adduct)}(molar ratio) was found 0.6.

(Evaluations as Radical-Curable Resin):

The unsaturated carboxylate, as obtained in Example 1, 12 or Comparative Example 3, was uniformly mixed with the components as shown in Table 2 in the mixing ratios (weight parts) as shown in Table 2, thereby preparing a resin composition, which was then subjected to the following evaluations. The results are shown in Table 2.

(Viscosity):

The resin composition was placed into a 20-ml sample tube to measure the viscosity of the resin composition at 25° C. with an E type viscometer.

(Curability):

The resin composition was coated onto a zinc-phosphated steel sheet with a bar coater so that the wet thickness might be 15 μm. Next, the resultant coated steel sheet was exposed to light at a line speed of 15 m/minute and a one-time-irradiation length of 1.4 m using an ultraviolet irradiation device as equipped with a high-pressure mercury lamp of 80 W/cm (distance from light source: 10 cm). The surface of the resultant coating film was verified by finger touch to evaluate the curability from the number of times of the ultraviolet irradiation as needed until the tackiness had disappeared. The smaller the number of times of the ultraviolet irradiation is, the more excellent the curability of the resin composition is.

(Surface hardness):

A test piece (coating film) was prepared in the same way as of the above curability evaluation. The surface hardness was defined as the concentration code of a pencil that was the hardest of pencils that gave visible scratches to the surface of the test piece by less than 2-time scratching when the surface of the test piece was scratched 5 times with leads of pencils as provided with a load of 1 kg in accordance with the pencil scratch test which is specified in section 8.4.1 of JIS-K-5400 (1995). The thinner the concentration code of the pencil is, the higher the surface hardness is.

(Adhesion):

Coating films were prepared by carrying out the ultraviolet irradiation 10 times each under the same conditions as of the above curability evaluation except that the zinc-phosphated steel sheet was replaced with a poly(vinyl chloride) sheet. Then, cellulose adhesive tapes (produced by Nichiban Co., Ltd.) were attached onto the resultant coating films (attached area: 18 cm×20 cm) and then peeled off therefrom, and then the peeled states of the coating films were observed with the eye to evaluate them on the following standards:

TABLE 2

| | | Resin composition | | | Comparative resin composition | | |
|---|---|---|---|---|---|---|---|
| | | (1) | (2) | (3) | (1) | (2) | (3) |
| Mixing ratios/ weight parts | Unsaturated carboxylate of Example 1 | — | 30 | 30 | — | — | — |
| | Unsaturated carboxylate of Example 12 | 40 | — | — | — | — | — |
| | Unsaturated carboxylate of Comparative Example 3 | — | — | — | 40 | — | — |
| | Urethane acrylate *1 | 60 | 50 | — | 60 | 50 | — |
| | Poly(methyl methacrylate) *2 | — | — | 30 | — | — | 30 |
| | 2-Hydroxyethyl acrylate | — | — | — | — | 15 | 30 |
| | 2-Hydroxypropyl acrylate | — | — | 10 | — | 15 | 10 |
| | Triethylene glycol diacrylate | — | 20 | 30 | — | 20 | 30 |
| | Photopolymerization initiator *3 | 1 | 1 | 1 | 1 | 1 | 1 |
| Viscosity (poise) | | 9.7 | Un-measured | Un-measured | 25.3 | Un-measured | Un-measured |
| Curability (number of times) | | 4 | 1 | 2 | 10 | Not smaller than 5 | Not smaller than 5 |
| Surface hardness | | H | 2H | B | 3B | H | 3B |
| Adhesion | | ○ | ○ | ○ | X | ○ | ○ |

○: not peeled,
X: throughout peeled
*1 "UV-7550B" produced by Nippon Gosei Kagaku K.K.
*2 Average molecular weight = 20,000
*3 "Irgacure 184" produced by Ciba-Geigy AG As is evident from Table 2, if the resin composition (1) involving the use of the unsaturated carboxylate as obtained in Example 12 is compared with the comparative resin composition (1) comprising the same component combination as of the aforementioned resin composition (1) except to use the unsaturated carboxylate as obtained in Comparative Example 3, then the resin composition (1) has a low viscosity and becomes cured rapidly, and further a cured coating film resultant from this composition has a surface hardness enough to be put to practical use and further has excellent adhesion to substrates, while the comparative resin composition (1) has a high viscosity and is inferior in respect to the curability and the surface hardness of a cured coating film resultant from this composition, and further the adhesion of this coating film to substrates is low.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. An unsaturated carboxylate mixture, which comprises at least two unsaturated carboxylates, which are represented by the following general formula (1):

(1)

wherein:
R$^1$ and R$^2$ independently of each other represent a hydrogen atom or a saturated aliphatic hydrocarbon group;
R$^3$ represents a hydrogen atom, a methyl group, or a saturated aliphatic hydrocarbon group other than the methyl group;
n is an integer of not smaller than 1; and
X represents wherein:
R$^4$ to R$^9$ independently of each other represent a hydrogen atom or an alkyl group;
wherein the unsaturated carboxylate mixture comprises a 1-mol adduct of n=1 in general formula (1) and a 2-mol adduct of n=2 in general formula (1) and/or a 3-mol adduct of n=3 in general formula (1) as essential components;
wherein the ratio of the 1-mol adduct to the total of the 2-mol adduct and the 3-mol adduct satisfies the following inequality:

(1-*mol adduct*)/{(2-*mol adduct*)+3-*mol adduct*)} ≧ 1 (*molar ratio*).

2. A production process for an unsaturated carboxylate, which comprises the step of carrying out a reaction of an unsaturated carboxylic acid of general formula (2) below with an unsaturated oxirane of general formula (3) below using at least one catalyst selected from the group consisting of chromium compounds, manganese compounds, iron compounds, nickel compounds, zinc compounds, silver compounds, tin compounds, neodymium compounds, and lead compunds,
wherein the general formula (2) is:

(2)

wherein: R$^1$ and R$^2$ independently of each other represent a hydrogen atom or a group selected from the group consisting of hydrocarbon groups, halogen groups, a hydroxyl group, ether groups, sulfide groups, a nitrile group, an aldehyde group, a carboxyl group, a sulfonic acid group, ester groups, and amide groups; and
R$^3$ represents a hydrogen atom, a methyl group, or a group, other than the methyl group, selected from the group consisting of hydrocarbon groups, halogen groups, a hydroxyl group, ether groups, sulfide groups, a nitrile group, an aldehyde group, a carboxyl group, a sulfonic acid group, ester groups, and amide groups;
and wherein the general formula (3) is:

(3)

wherein: R$^4$ to R$^9$ independently of each other represent a hydrogen atom or an alkyl group.

3. A radical-curable resin composition, which comprises a radical-curable resin and further comprises at least the unsaturated carboxylate mixture as recited in claim 1 as a reactive diluent.

* * * * *